United States Patent [19]

Nishizawa

[11] Patent Number: 4,944,483
[45] Date of Patent: Jul. 31, 1990

[54] APPARATUS FOR FORMING FIBER REINFORCED SLAB GEL FOR USE IN ELECTROPHORESIS

[76] Inventor: Hideyuki Nishizawa, 1-5-1 Nakazto Kuta Ku, Tokyo, Japan

[21] Appl. No.: 288,527

[22] Filed: Dec. 21, 1988

[30] Foreign Application Priority Data

Dec. 22, 1987 [JP] Japan .............................. 62-324962

[51] Int. Cl.⁵ ...................... B29C 33/10; G01N 27/26
[52] U.S. Cl. ................................. 249/83; 204/299 R; 249/109; 249/110; 249/120; 249/121; 249/130; 249/141; 425/812
[58] Field of Search ....................... 425/117, 123, 812; 249/83, 109, 110, 120, 121, 126, 130, 131, 141; 204/299 R, 182.8

[56] References Cited

U.S. PATENT DOCUMENTS

| | | | |
|---|---|---|---|
| 3,767,560 | 10/1973 | Elevitch | 204/299 R |
| 4,169,036 | 9/1979 | Anderson et al. | 204/299 R |
| 4,416,761 | 11/1983 | Brown et al. | 204/299 R |
| 4,560,459 | 12/1985 | Hoefer | 204/299 R |
| 4,795,541 | 1/1989 | Hurd et al. | 204/299 R |

Primary Examiner—James C. Housel
Attorney, Agent, or Firm—Donald D. Mon; David O'Reilly

[57] ABSTRACT

An apparatus for forming a fiber reinforced slab gel for use in electrophoresis including a box shaped casing having a first groove at the center of an inner lower end surface, and a cover having a second groove for hermetically closing an open area of the casing. A plurality of slab gel forming plates are laminated in the casing with fiber reinforced cores interposed between adjacent slab gel forming plates. An aqueous solution of an organic monomer is poured into the casing through a pouring pipe in the cover and the monomer is polymerized to form the gel slabs. Air in the casing is vented to the outside when the monomer is introduced into the casing.

8 Claims, 2 Drawing Sheets 0,944,483

APPARATUS FOR FORMING FIBER REINFORCED SLAB GEL FOR USE IN ELECTROPHORESIS

FIELD OF THE INVENTION

This invention relates to an apparatus for forming a slab gel, more particularly a fiber reinforced slab gel for use in electrophoresis.

BACKGROUND OF THE INVENTION

An electrophoresis apparatus in which ionic substances are separated in an aqueous solution by using such separating carriers as a sheet of paper, a cellulose acetate film starch gel, polyacrylamide gel or the like is widely used as means for separating proteins, enzymes, or the like.

One such slab gel electrophoresis apparatus, can separate a plurality of samples by using a single slab gel and has excellent separating performance.

This type of electrophoresis apparatus is widely used. In this apparatus, a polyacrylamide monomer is polymerized in a gap formed between two glass plates on stainless slab plates (slab gel forming plates) to form slab gel, and the separation of the samples is performed according to a predetermined procedure while holding the gel between the slab gel forming plates.

Such a procedure is done because the mechanical strength of the polyacrylamide gel slab formed in the gap between the slab gel forming plates is low, so that it is difficult to take out the slab gel from between the slab gel to separate the samples. However, unless the naked slab gel is used it is impossible to color the slab gel for confirming a separated state, so it is necessary to take out the slab gel from between the slab gel forming plates for coloring.

When a plurality of slab gels are preformed and it is desired to take one out for practical use, it is necessary to prepare a number of slab forming plates to form and store a number of slab gels in the gaps between the slab gel forming plates. However, the vessel utilized to store the slab gel is complicated in construction, expensive and uneconomical.

On the other hand, a slab reinforced by fibers of nonwoven polyester cloth as a reinforcing core not only has excellent mechanical strength but also has high dimensional stability so that it is possible to take the slab gel out from between two slab gel forming plates. The slab gel can be stored and the naked slab gel used for a separation operation. Consequently, it is not necessary to prepare a plurality of vessels for storing slab gels so that it is now possible to perform and store a plurality of slab gels. In addition, a slab gel reinforced with fibers as described above can be rinsed with purified water during storage and can be desalted before an actual separation operation by passing electric current through the slab gel, thus providing a novel method of use of the slab gel not considered in the past.

A slab gel reinforced with the fibers of nonwoven cloth described above can be manufactured by disposing in parallel two slab gel forming plates with a spacer interposed therebetween, pouring a polyacrylamide monomer solution into the gap between the slab gel forming plates together with a nonwoven cloth and then polymerizing the monomer solution.

With this method, however, air bubbles are entrained in the monomer solution, and oxygen in the air bubbles can prevent a polymerization reaction so that a porous slab gel is formed not suitable for separating samples. To prevent this disadvantage, it is necessary to prewet the nonwoven cloth with the polyacrylamide monomer solution. To this end the nonwoven cloth must be carefully bonded to the slab gel forming plates to prevent entraining air bubbles, which are troublesome and cause low productivity.

BRIEF DESCRIPTION OF THE INVENTION

Accordingly, it is an object of this invention to provide a novel apparatus for forming a fiber reinforced gel for use in electrophoresis capable of efficiently forming a solid, pore free slab gel.

According to this invention, an apparatus is provided for forming a fiber reinforced slab gel for use in electrophoresis, comprised of a box shaped casing having a first groove at the center of an inner lower surface, a cover for hermetically closing an opening in the casing, the cover being formed with a second groove on the inner surface thereof. A pouring pipe opens at a point above the inner lower surface for pouring an aqueous solution of organic monomer material into the casing, which when polymerized forms the gel slab. An air vent provided through the cover opens at a point near the upper end of the second groove, and a plurality of slab forming plates are laminated in the casing with reinforcing cores interposed between adjacent slab forming plates. One of the slab forming plates facing the inner surface of the cover extends to the upper end of the second groove.

The reinforcing cores are made of nonwoven cloths impregnated with the aqueous monomer solution. When the monomer is polymerized the reinforcing cores are converted into fiber reinforced slab gels.

Elongated spacers are interposed between the slab gel forming plates at both ends of the reinforcing cores to separate the plates.

The above and other features of the invention will be fully understood from the following detailed description and the accompanying drawings, in which:

DESCRIPTION OF THE PREFERRED EMBODIMENT

Figure 1:
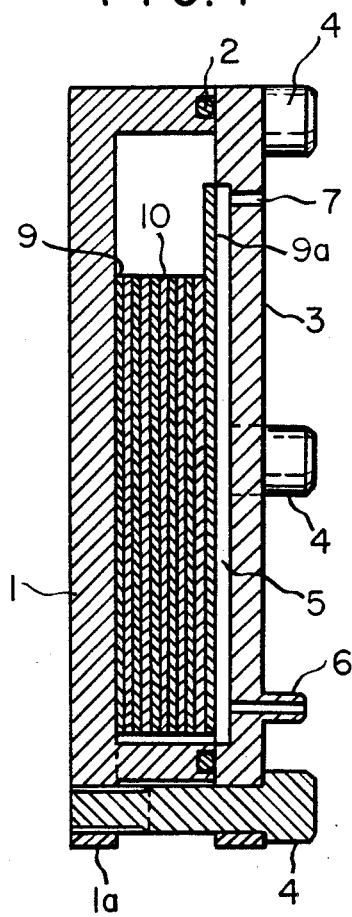
FIG. 1 is a longitudinal sectional view showing one embodiment of this invention.
Figure 2:
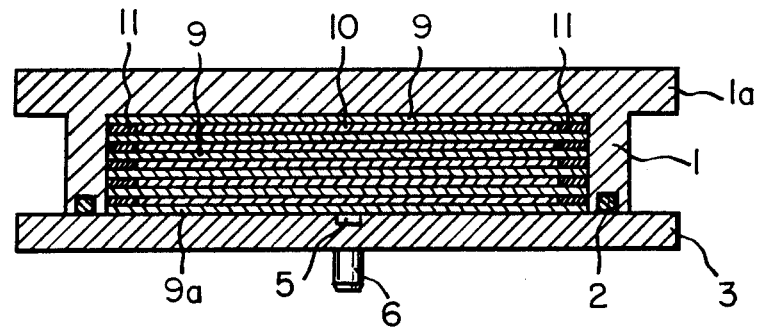
FIG. 2 is a cross-sectional view of the embodiment shown in FIG. 1.
Figure 3:
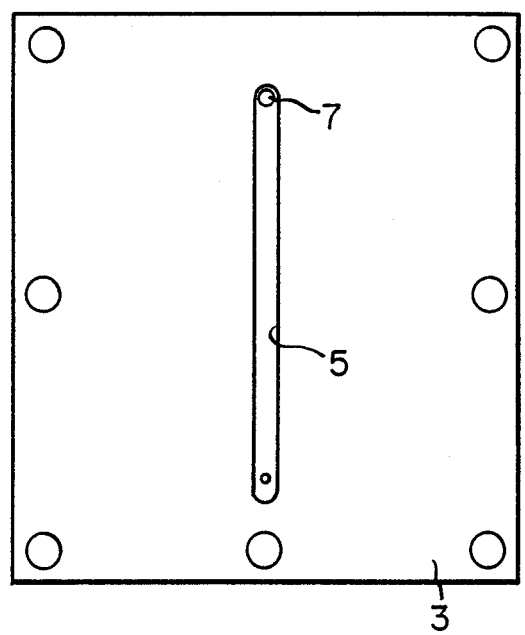
FIG. 3 is a plan view showing a casing cover for the embodiment of FIG. 1.
Figure 4:
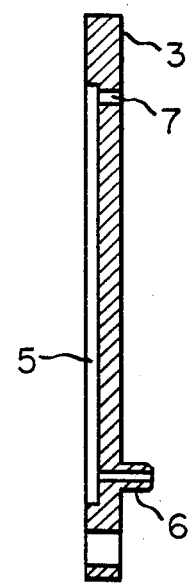
FIG. 4 is a longitudinal sectional view of the cover shown in FIG. 3.
Figure 5:
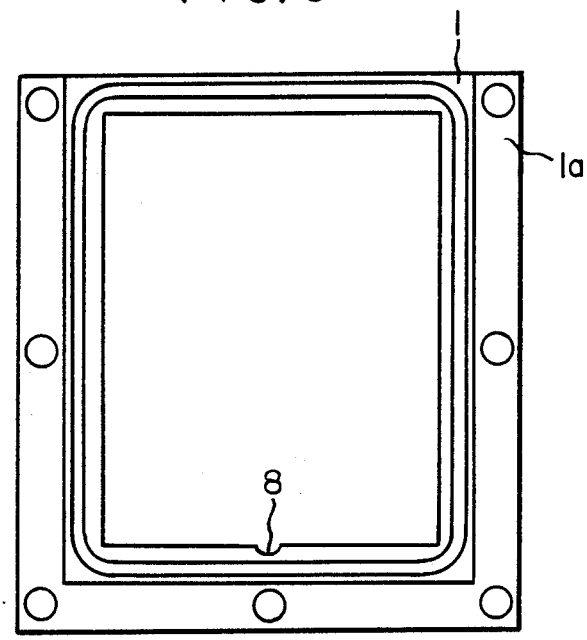
FIG. 5 is a plan view of the casing.
Figure 6:
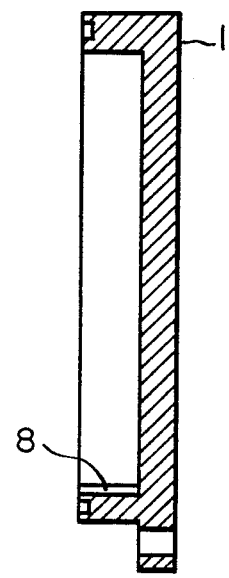
FIG. 6 is a longitudinal sectional view of the casing shown in FIG. 5.

In the preferred embodiment of the invention shown in the accompanying drawings, a substantially square shaped casing is provided for forming gel slabs or films, and a cover 3 is secured to the opening of the casing and sealed with "O" ring 2. Three flanges 1a are projected from three bottom sides of the casing 1. Cover 3 is constructed with the same plan configuration as the casing 1 including the projected flanges 1a. Cover 3 is secured to the casing 1 by bolts 4 threaded into flanges 1a. On the inner surface of the cover 3 a straight groove 5 is formed extending along the center line of the cover 3. The lower end of the groove is aligned with the lower inner surface of the casing, while the upper end of the groove terminates at a point slightly below the upper inner surface of the casing.

Cover 3 is provided with an aqueous solution pouring pipe 6 opening at a point slightly above the lower end of the groove 5. Further, an air vent opening 7 is provided for the cover near its upper end. Semi-circular groove 8 is provided at the center of the lower inner surface of the casing 1 to extend in the depth direction thereof.

A plurality of slab gel forming plates 9 are stacked in the casing 1 with reinforcing covers 10 made of nonwoven cloth interposed between the slab gel forming plates. The length of the slab gel forming plates is shorter than the distance between the lower inner surface of the casing and the upper end of groove 5, except plate 9a that contacts the inner surface of the cover. Furthermore, elongated rectangular spacers 11 are disposed between both ends of respective slab gel forming plates 9 and the inner surface of the casing 1. The reinforcing cores 10 are constructed to have substantially the same configuration as the slab gel forming plates 9. Slab gel forming plate 9a in contact with the inner surface of the cover 3 is constructed with its upper end at the same level as the upper end of the groove 5 provided for the cover 3.

The apparatus described above is used for forming and manufacturing fiber reinforced gel for use in electrophoresis in the following manner. At the time of assembling the apparatus, a plurality of slab gel forming plates 9 and 9a are loaded in the casing 1 with reinforcing cores 10 interposed between respective slab gel forming plates. Elongated spacers 11 are disposed on both ends of the cores 10. Cover 3 is then applied and secured to the casing using bolt 4.

Then a small quantity of organic solvent, for example about 3 or 5 ml of isopropanol, is poured into casing 1 through pouring pipe 6. The organic solvent poured in enters the casing through pouring pipe 6, and grooves 5 and 8, to wet the lower ends of laminated reinforcing cores 10. The organic solvent impregnates the lower ends of the reinforcing cores 10.

An aqueous solution of a polyacrylamide monomer for forming polyacrylamide films is then poured into the casing.

Air entering the casing together with the aqueous solution of polyacrylamide monomer poured through pouring pipe 6 is separated from the aqueous solution at the inner end of pouring pipe. The separated air rises through groove 5 and is then discharged to the outside of casing 1 through vent opening 7. As a consequence, the quantity of air remaining in the casing is very small. The aqueous solution of the polyacrylamide monomer free from air reaches the lower ends of the reinforcing cores 10 in the same manner as the organic solvent to surround the reinforcing cores and push the organic solvent upwards.

Since the quantity of air remaining in the casing is very small and the aqueous solution of polyacrylamide monomer pushes the organic solvent upward, the polyacrylamide monomer permeates the reinforcing cores and adheres to the surfaces thereof and does not contain any air bubbles. Thus, slab gels obtained by polymerizing the polyacrylamide monomer supported by the reinforcing cores do not contain any air and is free from pores.

Finally, the casing is disassembled to take out the resulting gel films.

The nonwoven cloths normally used are generally made of such chemical fibers as nylon or polyester fibers. The surface of these chemical fibers generally has low affinity to water but high affinity to organic solvents. Among organic solvents, alcohols having a high affinity to water and can be admixed with water at any ratio and, having a smaller specific gravity than water, enhance permeability of the aqueous solution into the nonwoven fabrics. Consequently, where the lower alcohol permeates the nonwoven cloth and the aqueous solution of the polyamide monomer is added, the lower alcohol assists permeation of the aqueous solution in to the nonwoven cloth.

The acrylamide monomer utilized to form gel films has a conventional composition, that consists of 5 g of acrylic amide, 0.25 g of $N_1N^1$ — methylene bisacrylamide, 0.05 ml of $N_1N^1$ — tetramethlethylene diamine, and 0.05 g of ammonium peroxide which are dissolved in 100 ml of water. The organic solvent admitted prior to the pouring of the aqueous solution of polyacrylamide monomer is selected from the group consisting of alcohol including isopropanol, methanol, ethanol, propanol, tertiary butanol, ketones including acetone, and ethers including dioxane. However, any other material can be used that has a high affinity to water and not to nonwoven cloths that constitute the reinforcing core, that can be expelled from the reinforcing core at the time of pouring the aqueous solution of polyacrylamide monomer, and not influenced by the pH of the aqueous solution.

It should be understood that the invention is not limited to the embodiment described above. For example, it is not always necessary to introduce an organic solvent before pouring in the aqueous solution of polyacrylamide monomer.

With the apparatus of this invention it is possible to form solid fiber reinforced slab gels without pores which have sufficient mechanical strength.

This invention is not to be limited by the embodiment shown in the drawings and described in the description, which is given by way of example and not of limitation, but only in accordance with the scope of the appended claims.

What is claimed is:

1. Apparatus for forming gel slabs for use in electrophoresis comprising:
   a box shaped casing, having an open vertical side and a first horizontal groove centrally located in an inner lower end surface thereof;
   a cover hermetically closing said open vertical side of said casing;
   said cover having an upwardly extending second groove located on a surface thereof facing said casing with a lower end aligned with said first groove;
   a pouring pipe in the lower end of said second groove and above said first groove for pouring an aqueous solution of organic monomer material into said casing, which when polymerized forms said gel slabs;
   an air vent in the upper end of said second groove;
   a plurality of spaced apart slab forming plates vertically stacked in said casing, one of said plates abutting the inner surface of said cover and extending to the upper end of said second groove.

2. The apparatus according to claim 1 including elongated spacers disposed between adjacent slab forming plates along opposite ends thereof for separating said slab forming plates.

3. The apparatus according to claim 1 including an organic solvent disposed in said casing for wetting lower ends of slab reinforcing cores to be located between adjacent plates.

4. Apparatus for forming gel slabs for use in electrophoresis, comprising:
   a box shaped casing having an open vertical side;
   a first groove in a lower inner end surface of said box shaped casing extending inwardly from said open vertical side;
   cover means constructed to cover said open vertical side and hermetically seal said box shaped casing;
   an upwardly extending second groove located on a surface of said cover means facing said casing with a lower end of said second groove aligned with said first groove;
   a pouring pipe in the cover means at the lower end of said second groove for receiving an aqueous solution of organic monomer material poured into said box shaped casing which when polymerized forms said gel slabs;
   an air vent through said cover means at an upper end of said second groove;
   a plurality of spaced apart slab forming plates stacked substantially vertically in said box shaped casing;
   one of said slab forming plates abutting an inner surface of said cover and extending to the upper end of said second groove.

5. The apparatus according to claim 4 including elongated spacers disposed between adjacent slab forming plates along opposite sides thereof for separating said slab forming plates.

6. The apparatus according to claim 4 including an organic solvent disposed in said box shaped casing for wetting lower ends of said slab reinforcing cores to be positioned between adjacent plates.

7. The apparatus according to claim 6 in which said organic solvent is an alcohol selected from the group consisting of isopropanol, methanol, ethanol, propanol, and tertiary butanol.

8. The apparatus according to claim 6 in which said organic solvent is selected from the group consisting of acetone and dioxane.

* * * * *